United States Patent [19]
Hosoda

[11] Patent Number: 6,008,466
[45] Date of Patent: Dec. 28, 1999

[54] LASER BEAM MACHINING DEVICE WITH PROTECTIVE MASK AND SAFETY SWITCHES

[75] Inventor: Naoyoshi Hosoda, Tokyo, Japan

[73] Assignee: Nihon Welding Co., Ltd., Tokyo, Japan

[21] Appl. No.: 09/093,432

[22] Filed: Jun. 8, 1998

[30] Foreign Application Priority Data

Feb. 10, 1998 [JP] Japan .................................. 10-028335

[51] Int. Cl.⁶ .................................................. B23K 26/00
[52] U.S. Cl. ............................... 219/121.62; 219/121.63; 219/147; 2/8
[58] Field of Search ........................... 219/121.6, 121.62, 219/121.63, 147; 2/8

[56] References Cited

U.S. PATENT DOCUMENTS

| | | | |
|---|---|---|---|
| 2,761,046 | 8/1956 | Herrick et al. ........................... | 219/147 |
| 3,392,259 | 7/1968 | Meier .................................. | 219/121.75 |
| 3,622,743 | 11/1971 | Muncheryan ....................... | 219/121.63 |
| 3,692,974 | 9/1972 | Thomason et al. ..................... | 219/147 |
| 3,719,793 | 3/1973 | Finger ..................................... | 219/147 |
| 4,237,364 | 12/1980 | Lemelson ............................ | 219/121.63 |
| 4,679,255 | 7/1987 | Kuhlman ........................................... | 2/8 |
| 4,937,879 | 7/1990 | Hall et al. ............................ | 219/147 X |
| 5,189,735 | 3/1993 | Corona ............................................. | 2/8 |

FOREIGN PATENT DOCUMENTS

| | | |
|---|---|---|
| 7-124767 | 5/1995 | Japan . |
| 8-19880 | 1/1996 | Japan . |
| 9-99381 | 4/1997 | Japan . |
| 9-220690 | 8/1997 | Japan . |

*Primary Examiner*—Gregory Mills
*Attorney, Agent, or Firm*—Oppenheimer Wolff & Donnelly LLP

[57] ABSTRACT

A protective mask which has a face shield and an eye shield is used for safety when a worker machines a workpiece by a laser beam. Start switches are provided in the mask, and closed when a worker wears the mask. A laser torch, a conductive clip and a laser oscillator are connected in series. When a workpiece is brought in contact with the end of a taper nozzle of the laser torch and the conducting clip, an electric current is sent from a power source to the laser oscillator, which is oscillated. Thus, accident by laser beam owing to unexpected electric conduction is prevented.

13 Claims, 5 Drawing Sheets

LASER BEAM MACHINING DEVICE WITH PROTECTIVE MASK AND SAFETY SWITCHES

BACKGROUND OF THE INVENTION

The present invention relates to a laser beam machining device in which a laser beam is guided by optical fibers to machine a workpiece.

In a laser beam machining device where a laser beam generated by a laser oscillator is introduced to a workroom via optical fibers to conduct machining such as cutting and welding, it is necessary to focus the laser beam exactly at any time to a workpiece.

The laser beam provides large energy and needs much care to safety. Thus, a laser torch is generally moved by an automatic device, keeping a distance to the workpiece to be machined. Further, if the laser beam is emitted from a laser torch only when a worker wears a protective mask exactly, safety will be increased.

In order to move the laser torch while a predetermined distance to the workpiece is kept by the automatic device, the device becomes larger and complicate, and is expensive. Further, it is difficult to handle, and has very low efficiency to machine a small amount of workpieces.

BRIEF DESCRIPTION OF THE DRAWINGS

The features and advantages of the invention will become more apparent from the following description with respect to embodiments as shown in appended drawings wherein.

SUMMARY OF THE INVENTION

An object of the present invention is to provide a laser beam machining device which machines a workpiece safely and easily. According to the present invention, there is provided a laser beam machining device, comprising:

a laser oscillator for generating a laser beam;

optical fibers connected to said laser oscillator to guide the laser beam;

a laser torch which comprises a pipe which has a taper nozzle at a front end, a going-out end of said optical fibers being provided in the pipe so that the laser beam from the going-out end is focused in the vicinity of an end of the taper nozzle;

conducting means for passing an electric current to a workpiece;

a protective mask which has a face shield which a worker wears; and a start switch which is connected to said laser oscillator, said start switch being closed when the worker wears said face shield and when the end of the taper nozzle and said conducting means are brought into contact with the workpiece, to pass the electric current to said laser oscillator from a power source to oscillate said laser oscillator.

When the worker wears the protective mask exactly and when the end of the laser torch is brought into contact with the workpiece, the laser beam is automatically generated, thereby facilitating operation and assuring safety without emitting the laser beam unexpectedly.

DETAILED DESCRIPTION OF PREFERRED EMBODIMENTS

Figure 1:
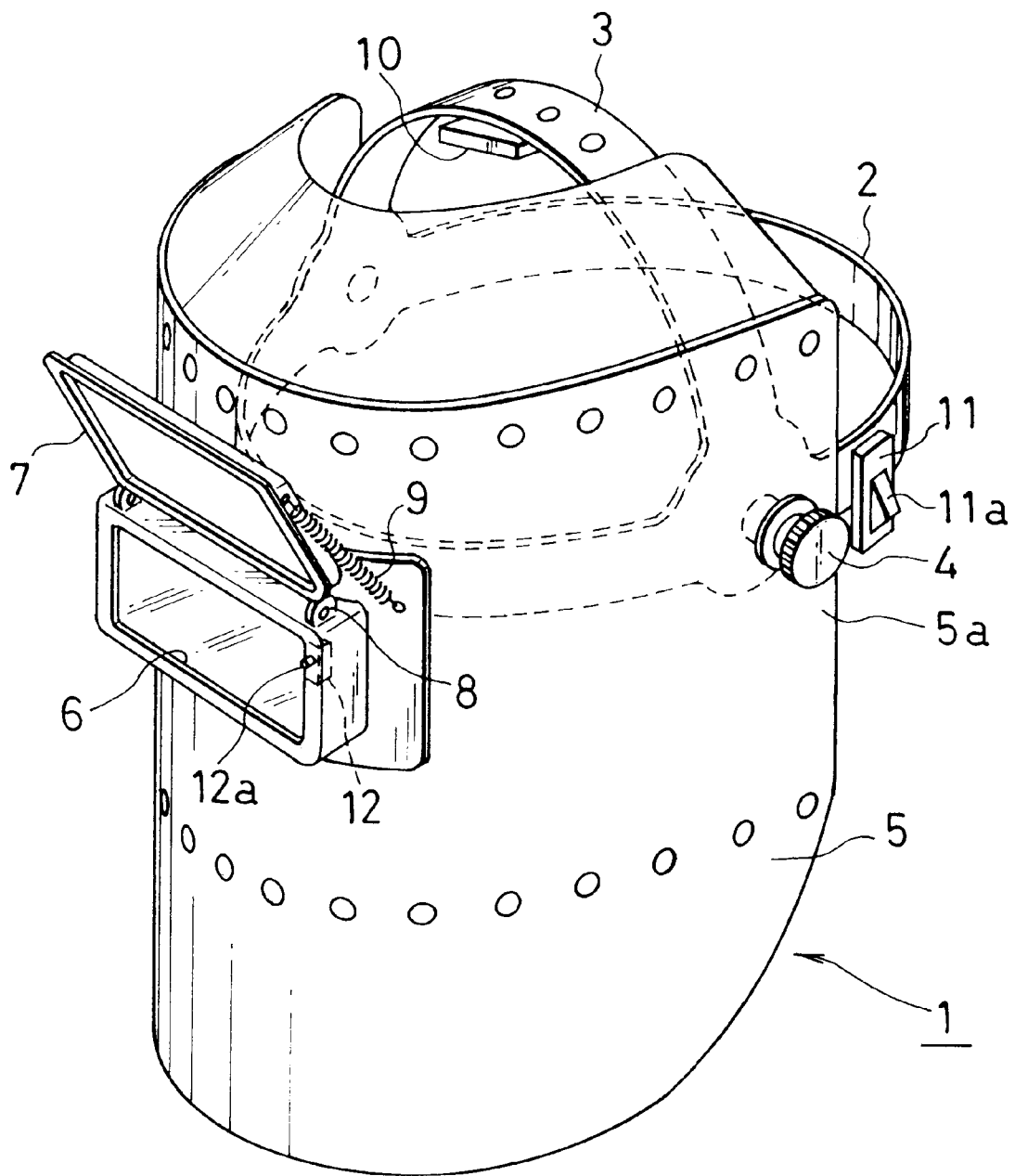
FIG. 1 is a perspective view of a protective mask in a laser beam machining device according to the present invention.

FIG. 1 is one embodiment of a welding protective mask 1 according to the present invention.

The protective mask 1 comprises an engagement ring 2 which can be engaged over a head of a worker; a suspension band 3 which is integrally connected with the engagement ring 2; and a face shield 5 which is pivoted about pivots 4 to the engagement ring 2 to cover the upper surface of the head of the worker.

On the front surface of the face shield 5, an eye window frame 6 is provided, and the upper edge of an opening eye shield 7 is pivoted above the eye window frame 6 about pivots 8. A tension spring 9 is mounted between the side of the eye shield 7 and the front surface of the face shield 5 slightly lower than the pivot 8. If the eye shield 7 is fully opened or closed, such a fully opened or closed condition of the eye shield 7 is elastically maintained by stretching the tension spring 9.

On the lower surface of the middle of the suspension band 3, a push-button prior switch 10 is mounted. When the worker wears the suspension band 3, the prior switch 10 is pressed and closed by the top of his head. Behind one of the pivots 4, a first start switch 11 which contains an inclined piece 11a is mounted. When the face shield 5 is turned upwards about the pivot 4, the inclined piece 11a of the first start switch 11 is pressed by the side end 5a of the face shield 5, and the first start switch 11 is opened. When the face shield 5 is turned downwards to cover a face of the worker, the inclined piece 11a is projected without being pressed and contacts of the first start switch 11 is closed.

On the inside of the side wall of the eye window frame 6, a second start switch 12 which comprises a microswitch is mounted. When the eye shield 7 is opened upwards, it gets away from an operative projection 12a of the second start switch 12 and the second start switch 12 is opened. When the eye shield 7 is closed, the operative projection 12a is pressed and the second start switch 12 is closed.

The prior switch 10, the first start switch 11 and the second start switch 12 are connected in series and closed to prepare welding. The details thereof follow.

Figure 2:
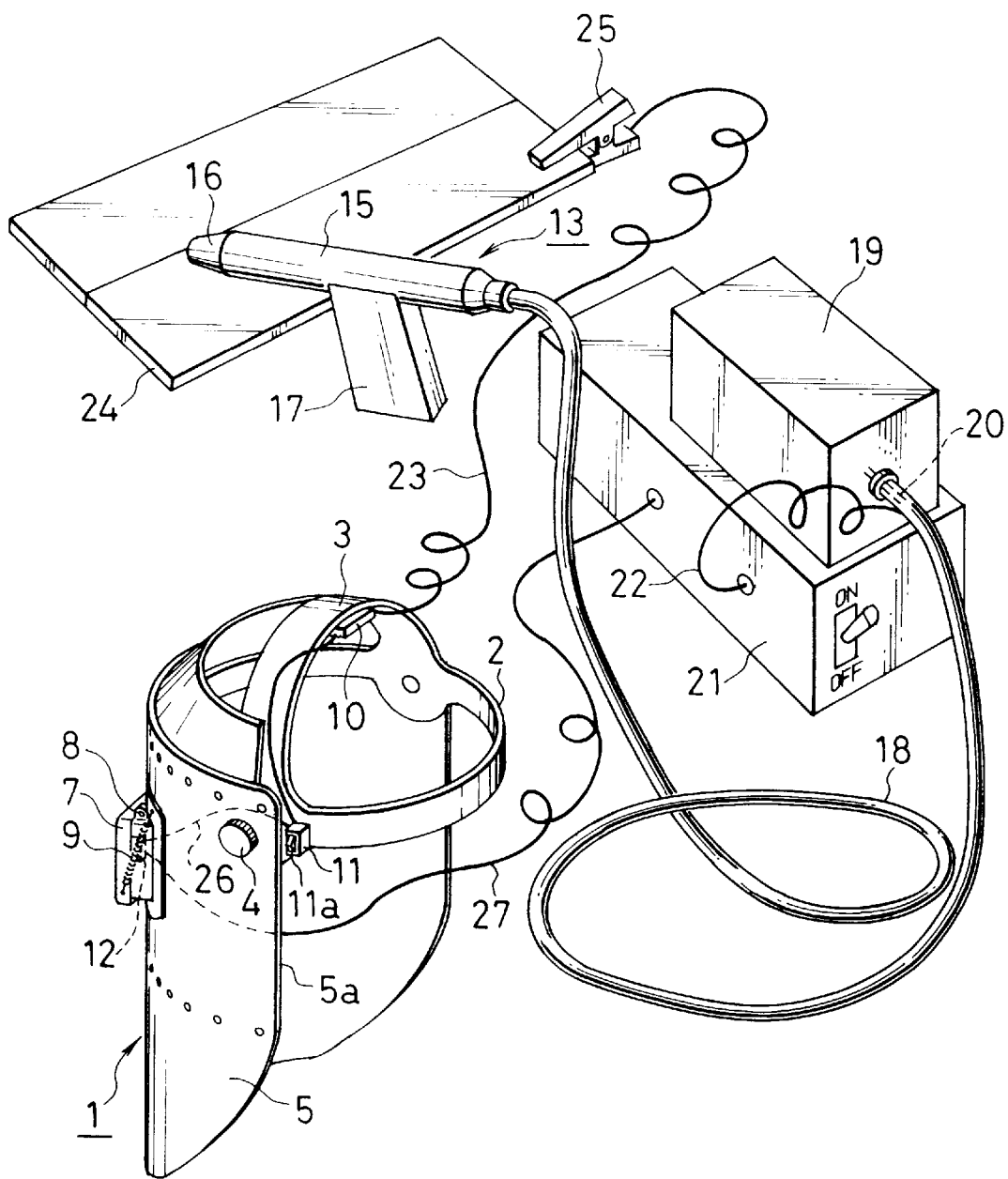
FIG. 2 is a perspective view which shows the first embodiment of a laser beam machining device according to the present invention.
Figure 3:
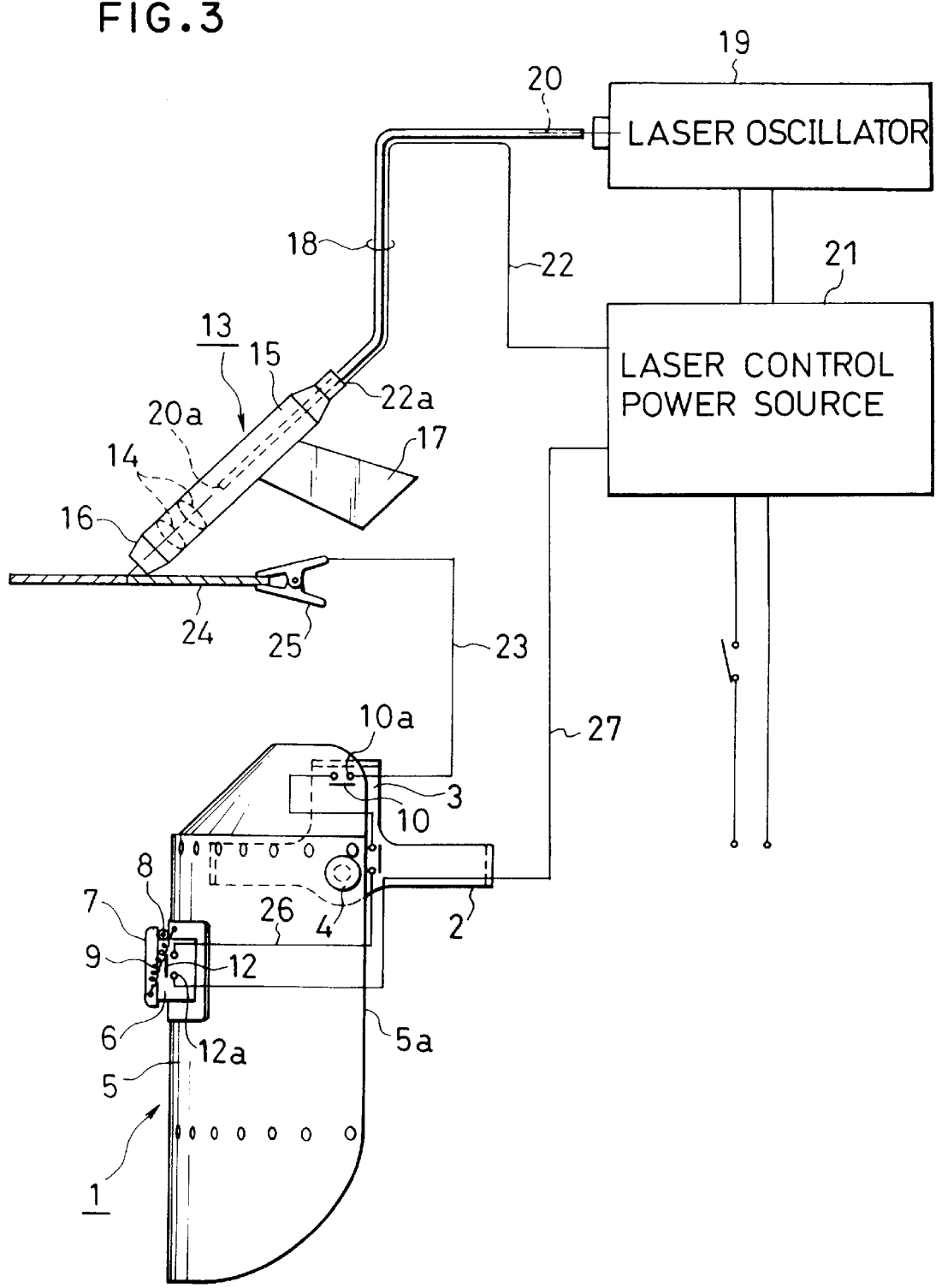
FIG. 3 is a circuit diagram of the first embodiment in FIG. 2.

FIG. 2 is a perspective view which illustrates the first embodiment of a laser beam machining device according to the present invention which contains the foregoing protective mask 1, and FIG. 3 is a circuit diagram of the first embodiment.

The numeral 13 in FIGS. 2 and 3 denotes a laser torch in which a taper nozzle 16 is provided in the front portion of a pipe 15 in which a suitable condenser lens 14 is provided, a handle 17 extending perpendicular to an axis of the pipe 15. In the pipe 15, a flexible tube 18 is inserted from the rear end. In the flexible tube 18, optical fibers 20 from a laser oscillator 19 and a control line 22 from a laser control power source 21 are inserted. A going-out end 20a for the optical fibers 20 is positioned right behind the condenser lenses 14 in the pipe 15. The end 22a of the control line 22 is connected to the pipe 15.

At the end of a lead 23 from an output contacting point 10a of the prior switch 10 of the protective mask 1, a conducting clip 25 which can hold a metal workpiece 24 is secured.

The prior switch 10, the first start switch 11 and the second start switch 12 are connected with a lead in series, and an input contacting point 12a of the second start switch 12 is connected to the laser control power source 21 via a lead 27.

The operation thereof will be described as below.

After the workpiece 24 is clipped by the conducting clip 25, the worker puts on the protective mask 1 and the prior switch 10 is closed by the top of his head. Then, the face shield 5 and the eye shield 7 are turned downwards, so that the switches 10, 11 and 12 are closed and connected to the laser control power source via a lead 27. The end of the tapered nozzle 16 of the pipe 16 of the laser torch 13 is brought into contact with a welding portion of the workpiece 24. A circuit for the laser control power source 21 is made, and an electric current is forwarded to the laser oscillator 19, which is thus actuated to generate a laser beam.

The laser beam is emitted from the end 20a of the optical fibers 20, and focused at a portion to be welded on the workpiece 24. The laser torch 13 is moved on the workpiece 24, thereby assuring easy safety welding.

Without mounting the prior switch 10 for making a circuit for the laser control power source on the suspension band 3 of the protective mask 1, the prior switch 10 may be mounted to the handle 17 of the laser torch 13 or at a position which is far from the protective mask 1.

Figure 4:
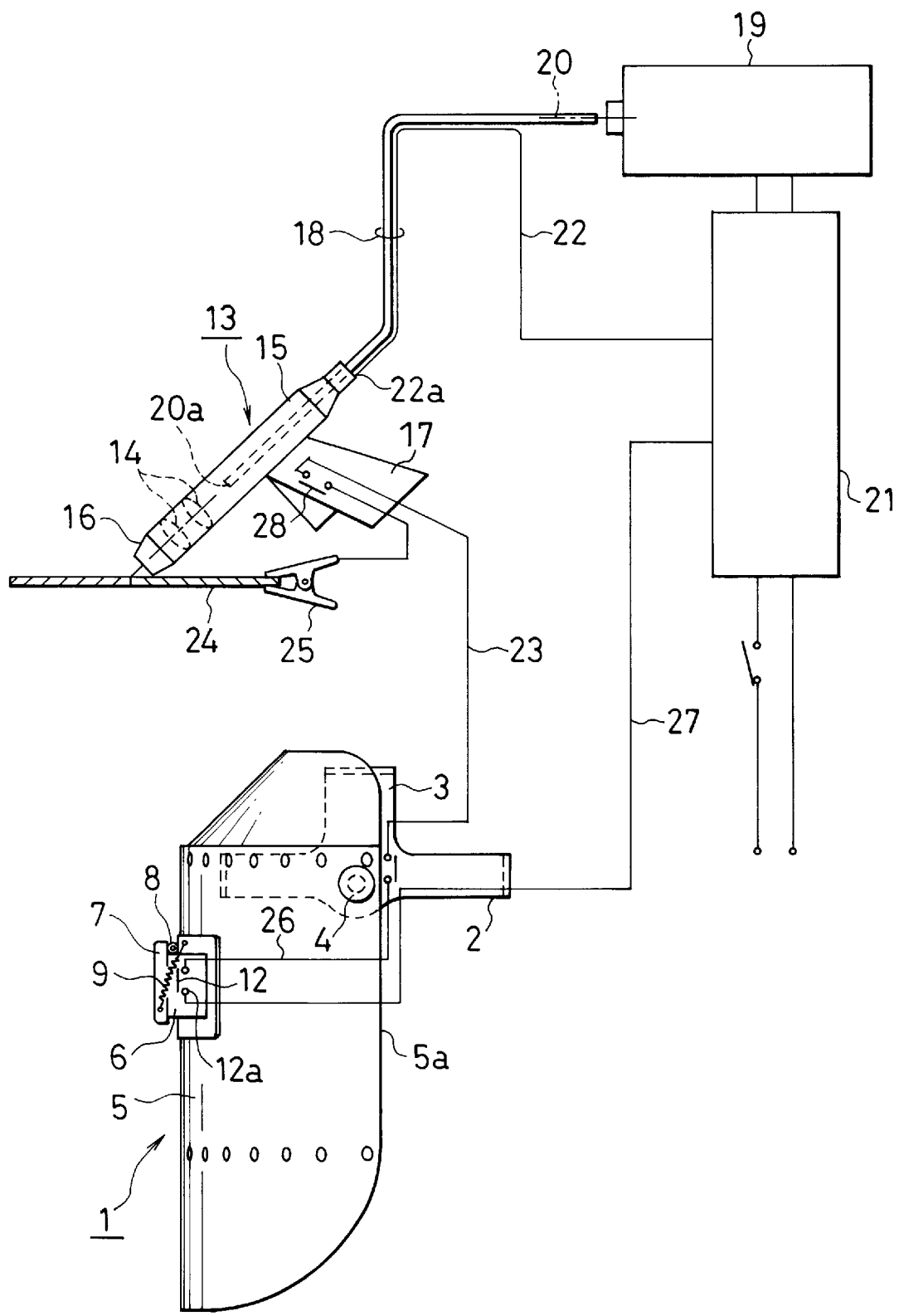
FIG. 4 is a circuit diagram of the second embodiment of the present invention.

In the second embodiment as shown in FIG. 4, the protective mask 1 has no prior switch in the middle of the lower surface of the suspension band 3 as shown in FIGS. 2 and 3, but a trigger-type prior switch 28 is mounted to a handle 17 of the laser torch 13. In FIG. 4, the same numerals are allotted to the same members in FIGS. 2 and 3, and description thereof is omitted. The conducting clip 25 and the first start switch 11 are connected via the trigger-type prior switch 28 on the handle 17. The others are similar to those in FIGS. 2 and 3. Compared with the prior switch 10 mounted to the suspension band 3 of the protective mask 1, the trigger-type prior switch 28 can be surely operated, and if operation does not begin, the laser oscillator 19 is not operated, thereby increasing safety.

In the foregoing embodiments, the first start switch 11 operated by closing the face shield 5 and the second start switch 12 operated by closing the eye shield 7 are connected in series to generate a laser beam, but only a single start switch may be provided.

Figure 5:
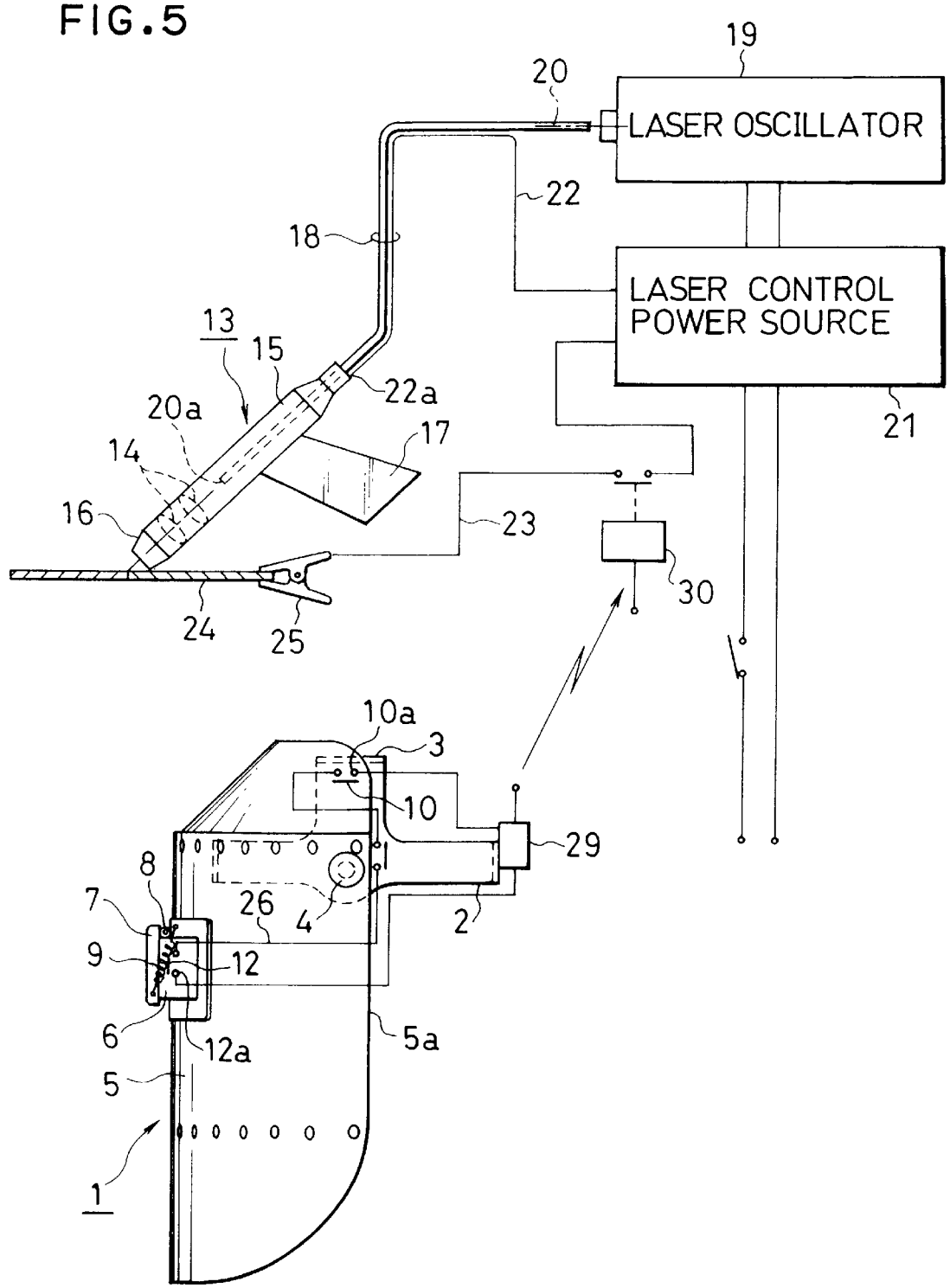
FIG. 5 is a circuit diagram of the third embodiment of the present invention.

The switches 10, 11 and 12 in the protective mask 1 may be connected to the laser control power source 21 wirelessly without the lead 27 in the third embodiment as shown in FIG. 5. There are a radio transmitter 29 in the lead 26 for connecting the switches 10, 11 and 12 of the protective mask 1, and a radio receiver 30 for receiving an electric wave from the radio transmitter 29 in the lead 23 for connecting the conducting clip 25 to the laser control source 21. The others are the same as those in FIG. 3. Thus, working efficiency is increased without wiring.

The foregoing merely relate to embodiments of the invention. Various modifications and changes may be made by persons skilled in the art without departing from the scope of claims wherein:

What is claimed is:

1. A laser beam machining device, comprising:
   a laser oscillator for generating a laser beam;
   optical fibers connected to said laser oscillator to guide the laser beam;
   a laser torch which comprises a pipe which has a taper nozzle at a front end, a going-out end of said optical fibers being provided in the pipe so that the laser beam from the going-out end is focused in the vicinity of an end of the taper nozzle;
   a conducting clip configured to clip a workpiece to enable passage of an electric current through the workpiece;
   a protective mask which a worker wears which further comprises a face shield and an eye shield the mask incorporating at least three switches, the switches comprising:
      a prior switch which is connected to said laser oscillator, said prior switch located so as to be actuated when the protective mask is placed on the worker's head and being closed when the worker wears said protective mask and face shield;
      a first start switch located so as to be actuated when the face shield is moved to a location protecting the face of the worker; and
      a second start switch actuated when the eye shield is moved to a closed position;
   operation of the laser oscillator being enabled when the prior switch and the first and second start switches are actuated so that the face mask is being worn and the face shield is down over the workers face and the eye shield is closed and when the end of the taper nozzle and said conducting clip are brought into contact with the workpiece, to initiate an enabled state allowing the passage of electric current to said laser oscillator from a power source to oscillate said laser oscillator.

2. The laser beam machining device as claimed in claim 1 wherein a condenser lens is provided in the pipe in front of the going-out end of the optical fibers so that the laser beam from the going-out end may be focused in the vicinity of the end of the taper nozzle.

3. The laser beam machining device as claimed in claim 1 wherein the start switch is opened by pivoting the face shield upwards and closed by the face shield downwards to cover a face of the worker.

4. The laser beam machining device as claimed in claim 1 wherein the prior switch, the first start switch and the second start switch are connected in series.

5. The laser beam machining device as claimed in claim 1 further comprising a trigger-type switch connected so that the laser oscillator is enabled only when the trigger-type switch is also actuated, which trigger-type switch is mounted on a handle of the laser torch.

6. The laser beam machining device as claimed in claim 1 wherein a radio transmitter is provided in a circuit for connecting the switches of the protective mask, and a radio receiver for receiving an electric wave from the radio transmitter is provided in a circuit for connecting the conducting means and the laser oscillator.

7. The laser beam machining device as claimed in claim 1 further comprising a radio transmitter provided in the circuit for the laser control power source connected to the first and second start switches of the protective mask; and a radio receiver for receiving an electric wave from the radio transmitter provided configured such that a condition where both the first and second start switches are closed will be indicated without need for a wiring connection to the protective mask.

8. The laser beam machining device as claimed in claim 7, wherein the pipe, trigger-type switch and connecting clip are connected in series with the laser control power source when the pipe is electrically connected with the conducting clip via the workpiece, and the circuit for the laser control power source further comprises a switch opened and closed in response to the electric wave received by the receiver and connected in series with said pipe trigger-type switch, connecting clip and laser control power source.

9. The laser beam machining device as claimed in claim 1, further comprising a circuit for the laser control power source including the prior switch the first and second start switches the conducting clip, and the pipe included in the laser torch, all connected in series with the laser control power source, and the circuit being completed when the pipe is electrically connected to the conducting clip via the workpiece, the prior switch is closed, and the first and second start switches are closed, thereby enabling electric current to be forwarded to the laser oscillator from the laser control power source.

10. The laser beam machining device of claim 9, further comprising a control line connecting the pipe and the laser control power source and a flexible tube, the control line being inserted with the optical fibers in the flexible tube.

11. A laser beam machining device, comprising:

a laser oscillator for generating a laser beam;

optical fibers connected to said laser oscillator to guide the laser beam;

a laser control power source;

a laser torch which comprises a pipe which has a taper nozzle at a front end, a going-out end of said optical fibers being provided in the pipe so that the laser beam from the going-out end is focused in the vicinity of an end of the taper nozzle and a handle, said pipe being electrically connected to the laser control power source;

a conducting clip which can clip a workpiece to pass an electric current to the workpiece;

a protective mask which a worker wears which has a face shield and an eye shield;

a first start switch which is opened by pivoting the face shield upwards and closed by pivoting the face shield downwards to cover a face of the worker; and a second start switch which is provided near the eye shield in the face shield, said second start switch being opened by pivoting the eye shield upwards and closed by pivoting the eye shield downwards, said first and second start switches being closed when the worker wears said face shield, when the eye shield is closed;

a trigger-type prior switch incorporated in the handle of the laser torch;

a circuit for the laser control power source comprising the pipe of the laser torch, the conducting clip, the trigger-type prior switch, and the first and second start switches;

the circuit for the laser control power source being configured so that when the end of the taper nozzle and said conducting clip are brought into contact with the workpiece, and the trigger-type prior switch and the first and second start switches are closed the laser control power source allows passage of electric current to said laser oscillator to oscillate said laser oscillator.

12. The laser beam machining device as claimed in claim 11 wherein a condenser lens is provided in the pipe in front of the going-out end of the optical fibers so that the laser beam from the going-out end may be focused in the vicinity of the end of the taper nozzle.

13. The laser beam machining device as claimed in claim 11, wherein the circuit for the laser control power source is connected in series with the laser control power source and the circuit is completed when the pipe is electrically connected to the conducting clip via the workpiece, the trigger-type prior switch is closed, and the first and second start switches are closed, thereby enabling electric current to be forwarded to the laser oscillator from the laser control power source.

* * * * *